United States Patent [19]

Alexander

[11] 4,105,766
[45] Aug. 8, 1978

[54] 4,5-DIHYDRO-5-OXOPYRAZOLO[1,5-A]QUINAZOLINE-3-CARBOXYLIC ACID DERIVATIVES

[75] Inventor: E. John Alexander, East Greenbush, N.Y.

[73] Assignee: Sterling Drug Inc., New York, N.Y.

[21] Appl. No.: 826,163

[22] Filed: Aug. 19, 1977

[51] Int. Cl.$^2$ .................. A61K 31/505; C07D 487/14
[52] U.S. Cl. ..................................... 424/251; 544/250
[58] Field of Search .................. 260/256.4 F; 424/251

[56] References Cited

U.S. PATENT DOCUMENTS

| | | | |
|---|---|---|---|
| 2,861,076 | 11/1958 | Knott et al. | 260/256.4 F |
| 3,313,815 | 4/1967 | Wolfe et al. | 260/256.4 F |
| 3,594,379 | 7/1971 | Hardtmann | 260/256.4 F |
| 3,862,191 | 7/1975 | El-Haj et al. | 260/256.4 F |

OTHER PUBLICATIONS

Wright, "J. Heterocyclic Chem.", vol. 6, 1969, pp. 947–948.

Primary Examiner—Donald G. Daus
Assistant Examiner—James H. Turnipseed
Attorney, Agent, or Firm—William G. Webb; B. Woodrow Wyatt

[57] ABSTRACT 4,5-Dihydro-5-oxopyrazolo[1,5-a]quinazoline-3-carboxylic acids and esters and alkali metal salts thereof, useful as anti-inflammatory, anti-allergic and anti-parasitic agents, are prepared by reacting a 4- or 5-$R_3$-2-carboxyphenylhydrazine with a lower-alkyl ethoxymethylenecyanoacetate and, if desired, saponifying the ester group and if desired, N-alkylating the product by reaction with an $R_2$-halide in the presence of an acid-acceptor.

53 Claims, No Drawings

4,5-DIHYDRO-5-OXOPYRAZOLO[1,5-A]QUINAZOLINE-3-CARBOXYLIC ACID DERIVATIVES

BACKGROUND OF THE INVENTION (a) Field of the Invention

This invention relates to 4,5-dihydro-5-oxopyrazolo[1,5-a]quinazoline-3-carboxylic acids and esters and alkali metal salts thereof useful as anti-inflammatory, anti-allergic and anti-parasitic agents.

(b) Description of the Prior Art

Wright, J. Heterocyclic Chem. 6, 947 (1969) discloses 4,5-dihydro-5-oxopyrazolo[1,5-a]quinazoline-3-carboxylic acid and the ethyl ester thereof. However, Wright discloses no utility for the compounds so described. In contrast, it has been found that certain compounds of the 4,5-dihydro-5-oxopyrazolo[1,5-a]quinazoline-3-carboxylic acid class possess useful anti-inflammatory, anti-allergic and anti-parasitic properties. In fact, it has been found that the acid disclosed by Wright also possesses anti-allergic activity.

SUMMARY OF THE INVENTION

In a composition of matter aspect, the present invention relates to certain 4-$R_2$-7- or 8-$R_3$-4,5-dihydro-5-oxopyrazolo[1,5-a]quinazoline-3-carboxylic acid and alkali metal salts of esters thereof which, depending upon the specific definitions of the $R_1$, $R_2$ and $R_3$ groups, are useful either as anti-inflammatory, anti-allergic and/or anti-parasitic agents.

The invention also relates, in a composition aspect, to a composition for treatment of allergic conditions comprising an effective anti-allergic amount of a 4-$R_2$-7- or 8-$R_3$-4,5-dihydro-5-oxopyrazolo[1,5-a]quinazoline-3-carboxylic acid or a lower-alkyl or pivaloyloxymethyl ester thereof in a pharmaceutical carrier.

In a process aspect, the invention relates to a process for preparing a lower-alkyl 7- or 8-$R_3$-4,5-dihydro-5-oxopyrazolo[1,5-a]quinazoline-3-carboxylate which comprises reacting a 4- or 5-$R_3$-2-carboxyphenylhydrazine with a lower-alkyl ethoxymethylenecyanoacetate.

In another process aspect, the invention relates to a process for preparing lower-alkyl 4-$R_2$-7- or 8-$R_3$-4,5-dihydro-5-oxopyrazolo[1,5-a]quinazoline-3-carboxylates which comprises reacting a lower-alkyl 7- or 8-$R_3$-4,5-dihydro-5-oxopyrazolo[1,5-a]quinazoline-3-carboxylate with an $R_2$ halide in the presence of an acid-acceptor.

DETAILED DESCRIPTION INCLUSIVE OF THE PREFERRED EMBODIMENTS

More specifically this invention relates to 4-$R_2$-7- or 8-$R_3$-4,5-dihydro-5-oxopyrazolo[1,5-a]quinazoline-3-carboxylic acids and lower-alkyl esters and alkali metal salts thereof having the formula:

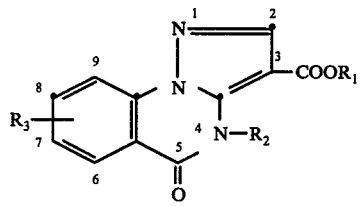

I where either:

A.

$R_1$ is hydrogen or an alkali metal cation;

$R_2$ is methyl, ethyl, lower-alkenyl or cyclopropylmethyl; and $R_3$ is hydrogen or 7- or 8-halo, except that when $R_1$ is hydrogen and $R_2$ is methyl, $R_3$ is not 7-fluoro.

which are useful as anti-inflammatory agents;

B.

$R_1$ is hydrogen, lower-alkyl or pivaloyloxymethyl;

$R_2$ is hydrogen, methyl, ethyl, lower-alkenyl, or cyclopropylmethyl;

$R_3$ is hydrogen, 7- or 8-methyl, 7- or 8-halo or 7-nitro, except that (a) when $R_1$ is lower-alkyl and $R_2$ is hydrogen, $R_3$ is not 8-methyl or 7-fluoro, (b) when $R_1$ is lower-alkyl and $R_2$ is methyl, $R_3$ is not 7-methyl or 7-bromo, (c) when $R_1$ is hydrogen and $R_2$ is methyl, $R_3$ is not 7-fluoro, and (d) when $R_1$ is hydrogen or lower-alkyl and $R_2$ is hydrogen, $R_3$ is not hydrogen, which are useful as anti-allergic agents, or

C.

$R_1$ is hydrogen or lower-alkyl;

$R_2$ is hydrogen or methyl; and $R_3$ is hydrogen, 7-methyl, 7-nitro, 7-amino, 7- or 8-chloro, 7-fluoro or 7-phenylthioureido ($C_6H_5NHCSNH$), except that (a) when $R_1$ is hydrogen or lower-alkyl and $R_2$ is hydrogen, $R_3$ is not hydrogen or 7-fluoro, and (b) when $R_1$ is lower-alkyl and $R_2$ is methyl, $R_3$ is not amino, which are useful as anti-parasitic agents.

The various excepting clauses above are included for the purpose of excluding from the ambit of the particular genus defined either known prior art species or species which have been found to be inactive for the particular purpose stated. Thus the excluding clauses under parts A. and B. (c) and under part B. (b) ($R_3$ is not 7-methyl) exclude two species found to be inactive as anti-inflammatory and/or anti-allergy agents. However these species have been found active as anti-parasitic agents and thus are within the ambit of part C. The compounds excluded under parts B. (a) (two species), B. (b) (one species where $R_3$ is not 7-bromo), and C. (b) (one species) have either been found inactive in all pertinent tests or have not been tested. Each of these four species however are useful as intermediates for preparing active species and are thus considered to be within the purview of the invention. The compounds excluded under parts B. (d) and C. (a) ($R_3$ is hydrogen) are disclosed in the prior art (Wright supra).

The compounds of formula I where $R_1$ is hydrogen are also useful as intermediates for the preparation of the corresponding amides which are prepared by conversion of the acids to the acid halide and reaction of the latter with an appropriate amine. The amides are disclosed in copending application Ser. No. 826,162, filed Aug. 19, 1977 and are useful as anti-secretory agents. In contrast, the instant compounds have been found to be inactive as anti-secretory agents.

As used herein the term lower-alkyl means a saturated, monovalent hydrocarbon radical, which may be straight or branched, containing from one to six carbon atoms, including methyl, ethyl, propyl, isopropyl, butyl, isobutyl, tertiarybutyl, hexyl and the like.

As used herein the term halo means fluoro, chloro or bromo.

As used herein the term lower-alkenyl means an unsaturated, aliphatic radical containing one double bond and having from three to five carbon atoms, including 1-(2-propenyl), 1-(2-methyl-2-propenyl), 1-(3-methyl-2-butenyl) and the like.

The compounds of formula I where $R_1$ is lower-alkyl, $R_2$ is hydrogen and $R_3$ is hydrogen, 7- or 8-methyl or 7- or 8-halo are prepared by reacting an appropriate 4- or 5-$R_3$-2-carboxyphenylhydrazine with a lower-alkyl ethoxymethylenecyanoacetate. The reaction is carried out in the presence of sodium acetate in an organic solvent inert under the conditions of the reaction, for example, dimethylformamide (hereinafter DMF), benzene, toluene, and the like. A preferred solvent is DMF, and it is preferred to carry out the reaction at a temperature in the range from 100° to 150° C. by heating a solution of the reactants in the solvent.

The 4- or 5-$R_3$-2-carboxyphenylhydrazines required as starting materials in the above-described procedure are prepared by diazotizing the corresponding 5- or 4-$R_3$-2-aminobenzoic acids with sodium nitrite in dilute mineral acid and reducing the resulting diazonium compound with bisulfite (aqueous sulfur dioxide).

The lower-alkyl ethoxymethylenecyanoacetates also required as starting materials are known compounds.

The compounds of formula I where $R_1$ is lower-alkyl; $R_2$ is methyl, ethyl, lower-alkenyl or cyclopropylmethyl and $R_3$ is hydrogen, 7- or 8-methyl or 7- or 8-halo are prepared by reacting the corresponding compounds of formula I where $R_2$ is hydrogen with an appropriate lower-alkyl, lower-alkenyl or cyclopropylmethyl halide in the presence of an acid-acceptor. The reaction is preferably carried out in an inert organic solvent, for example DMF or a lower-alkanol, at a temperature in the range from around 50° to 150° C.

The compounds of formula I where $R_3$ is 7-nitro are prepared by reacting the corresponding compounds where $R_3$ is hydrogen with sodium nitrate in concentrated sulfuric acid. The reaction is preferably carried out at ambient temperature, i.e. at a temperature in the range from about 15° to about 30° C.

The compounds of formula I where $R_3$ is 7-amino are prepared by catalytic reduction of the corresponding compounds where $R_3$ is 7-nitro. Reduction is effected with hydrogen in the presence of palladium-on-charcoal in an organic solvent, for example a lower-alkanol, or over Raney nickel in an alkaline medium in the presence of hydrazine hydrate.

The compounds of formula I where $R_3$ is 7-phenylthioureido are prepared by reacting the corresponding compounds where $R_3$ is 7-amino with phenyl isothiocyanate in pyridine. The reaction is carried out at a temperature in the range from about 80° to 100° C.

As indicated above the compounds of this invention have been found useful as anti-inflammatory, anti-allergic and anti-parasitic agents.

The compounds can be administered in the same manner as known anti-inflammatories, anti-allergics and anti-parasitics, i.e. parenterally or orally in any of the conventional pharmaceutical forms, as for instance, solutions, suspensions, tablets, capsules and the like.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation.

The test procedures used to determine the anti-inflammatory and anti-allergy activities of the compounds of the invention have been described in detail in the prior art as follows:

(1) The inhibition of carrageenin-induced foot edema test essentially described by Winter et al., Proc. Soc. Exp. Biol. and Med. 111, 544 (1962) as modified by Van Arman et al., J. Pharmacol. Exptl. Therap. 150, 328 (1965) and (2) a modification of the inhibition of adjuvant-induced arthritis test described by Pierson, J. Chronic Diseases 16, 863 (1963) and Glenn et al., Am. J. Vet. Res. 26, 1180 (1965), which were used to establish the anti-inflammatory activities of the compounds; and the passive cutaneous anaphylaxis test described by Mielens et al., Int. Arch. Allergy Appl. Immunol. 47, 633–649 (1974) which was used to establish the anti-allergy activity of the compounds.

Anti-parasitic activity of the compounds was shown by the following test procedures. Amoebacidal activity was shown in a test in which 100 or more female hamsters (Sprague-Dawley) weighing between 90 and 130 g. were individually weighed and sorted into groups of five animals each averaging either 100 ± 10 g. or 120 ± 10g. The test compounds (at least 200 mg.) and a reference standard, N,N'-(phenylenedimethylene)-bis[α,α-dichloro-N-(2-ethoxyethyl)acetamide] (FALMONOX®), were dissolved or suspended in 10 percent gelatin. The test compounds and the reference standard were administered to the naturally infected hamsters intragastrically via syringe in equally subdivided doses of 0.5 ml. 8 hours apart twice daily for 3 consecutive days, the test compounds being administered at a screening dose of 100 mg./kg./day and the reference standard being administered at a dose of 3.125 mg./kg./day. On the fourth day each of the test animals and the five hamsters receiving the reference drug, as well as non-medicated infected control animals, were killed and a portion of the mucus from the wall of the cecum was mixed in a drop of 0.85% sodium chloride. The preparation was examined under low power (100 X) of a compound microscope for the presence of motile trophozoites of *Entamoeba criceti*, and when a preparation was determined to be free from trophozoites, a second specimen was taken from another part of the cecum of the same animal and thoroughly examined before the animal was declared cleared of amoebas. Compounds were considered active when five of five hamsters were cleared of amoebas at 100 mg./kg./day for 3 days, of questionable or low activity when two, three of four of the five hamsters were cleared and inactive when zero or one of the five hamsters were trophozoite free. Results were recorded as a fraction: number of hamsters cleared/number of hamsters treated.

Trypanosomicidal activity of the compounds of the invention was determined in a test procedure in which albino female mice (Taconic Farms) weighing 20± 2 g. were intraperitoneally injected 3 days prior to initial medication with 0.2 ml. of an inoculum containing 500 *Trypanosoma brucei* organisms in 0.85% sterile saline. Blood for infecting purposes was obtained via cardiac puncture of a donor mouse previously determined to have a high parasitemia. Test medications to groups of five mice were started 3 days after infection at a time when the animals had begun to develop a rising blood parasitemia. The test compounds were suspended or dissolved in 10% autoclaved gelatin and administered orally in a volume of 0.2 ml. by gastric intubation in two equally subdivided daily doses 7 to 8 hours apart for 4 consecutive days. The total daily dose was 200 mg./kg.

Groups of 10 non-medicated infected control mice and five animals medicated with the reference compound LAMPIT® (tetrahydro-3-methyl-4-[(5-nitrofurfurylidene)amino]-2H-1,4-thiazine-1,1-dioxide) were included in each screening test. The test system is based on the survival of animals medicated with the test compound, and those mice alive at the end of 28 days post-infection were recorded as cured. (Non-medicated infected control mice rarely succumb later than 5 to 6 days post-innoculation with *T. brucei*). A compound was considered active if at least two of five animals survived until the termination of a 28 day post-infection holding period. The compound was considered of questionable activity if only one of five animals survived, and a compound was considered inactive if none of the animals survived to the end of the test.

The structures of the compounds of this invention were established by the modes of synthesis, by elementary analyses, and by ultraviolet, infrared and nuclear magnetic resonance spectra. The course of reactions and homogeneity of the products were ascertained by thin layer chromatography.

The manner and process of making and using the invention, and the best mode contemplated by the inventor of carrying out the invention will now be described so as to enable any person skilled in the art to which it pertains to make and use the same. The melting points are uncorrected.

Preparation of Intermediates

Preparation 1

A solution of 46.9 g. (0.31 mole) of 2-amino-5-methylbenzoic acid was prepared by adding 340 ml. of concentrated hydrochloric acid to a suspension of the former in 300 ml. of water. The solution was chilled to 0° C., and the cooled solution was treated dropwise with a solution of 21.6 g. (0.31 mole) of sodium nitrite in 210 ml. of water while maintaining the temperature below 3° C. When addition was complete the solution was stirred for an additional 15 minutes and then poured with stirring into a 12 liter flask containing 2.4 liters of water saturated with sulphur dioxide at 0°-5° C. while passing a vigorous stream of sulphur dioxide through the solution. The solution was stirred for an additional 30 minutes while bubbling sulphur dioxide through the mixture, and then allowed to stand for about 12 hours. The solution was then acidified with 3 liters of concentrated hydrochloric acid and cooled to 0°-5° C. The solid which separated was collected, washed twice with 50 ml. portions of dilute hydrochloric acid and dried to give 48.8 g. of 2-hydrazino-5-methylbenzoic acid hydrochloride, m.p. 194°-199° C.

Preparations 2-5

Proceeding in a manner similar to that described in Preparation 1 above, substituting for the 2-amino-5-methylbenzoic acid used therein an appropriate 5- or 4-$R_3$-2-aminobenzoic acid, the following 4- or 5-$R_3$-2-hydrazinobenzoic acids were similarly prepared:

Preparation 2

4-Methyl-2-hydrazinobenzoic acid hydrochloride (54 g., m.p. 184°-193° C.) prepared from 46.9 g. (0.31 mole) of 4-methyl-2-aminobenzoic acid and 21.6 g. of sodium nitrite;

Preparation 3

5-Chloro-2-hydrazinobenzoic acid hydrochloride (62.7 g., m.p. 200° C. dec.) prepared from 53.2 g. (0.31 mole) of 5-chloro-2-aminobenzoic acid and 21.6 g. of sodium nitrate;

Preparation 4

4-Chloro-2-hydrazinobenzoic acid hydrochloride (35.8 g., m.p. 187°-190° C.) prepared from 53.2 g. (0.31 mole) of 4-chloro-2-aminobenzoic acid and 21.6 g. of sodium nitrite; and Preparation 5

5-Fluoro-2-hydrazinobenzoic acid hydrochloride (48 g., m.p. 212°-215° C) prepared from 41.2 g. of 5-fluoro-2-aminobenzoic acid and 17.8 g. of sodium nitrite.

Preparation of Final Products

EXAMPLE 1

A solution of 50 g. (0.27 mole) of 2-hydrazinobenzoic acid hydrochloride [Pfanntiel et al., Ber. 75B, 1096-1107 (1942)], 45 g. (0.26 mole) of ethyl ethoxymethylenecyanoacetate and 26.4 g. (0.32 mole) of sodium acetate in 330 ml. of DMF was heated to 140° C., then cooled to ambient temperature, diluted with 130 ml. of water and chilled. The solid which separated was collected, washed with water, then with ethanol, then with diethyl ether and dried to give 62.6 g. of ethyl 4,5-dihydro-5-oxopyrazolo[1,5-a]quinazoline-3-carboxylate, m.p. 203°-205° C.

EXAMPLES 1A-1E

Following a procedure similar to that described in Example 1 above, substituting for the 2-hydrazinobenzoic acid hydrochloride used therein an appropriate 4- or 5-$R_3$-2-hydrazinobenzoic acid hydrochloride, the following compounds of formula I were similarly prepared, where in each case, $R_1$ is ethyl and $R_2$ is hydrogen. Here and elsewhere in the tables which follow, the weights of the starting materials (in this case the weight of the 2-hydrazinobenzoic acid hydrochloride) and the weights of the final products are given in the column headed "Wt.S.M./Wt.Prod.". The melting points of the final products and the solvent of recrystallization are given in the column headed "m.p.(° C.)/Solv.".

Table 1

| Example | $R_3$ | Wt.S.M./Wt.Prod. | m.p. (° C.)/Solv. |
|---|---|---|---|
| 1A | 7-$CH_3$ | 48.8 | 194-196 |
|  |  | 56.8 | tetrahydrofuran |
| 1B | 8-$CH_3$ | 53 | 208-212 |
|  |  | 64.8 | DMF/water |
| 1C | 7-Cl | 62.7 | 204-206 |
|  |  | 40.5 | tetrahydrofuran |
| 1D | 8-Cl | 35.8 | 283-286 (a) |
|  |  | 37.2 | DMF/water |
| 1E | 7-F | 47.5 | 193-196 |
|  |  | 59 | DMF/water |

(a) A small sample recrystallized from DMF alone gave m.p. 230-232° C.

EXAMPLE 2

A mixture of 4.1 g. (0.016 mole) of ethyl 4,5-dihydro-5-oxopyrazolo[1,5-a]quinazoline-3-carboxylate, 5 g. (0.036 mole) of finely powdered potassium carbonate and 5 ml. (0.08 mole) of methyl iodide in 35 ml. of DMF was stirred while heating on a steam bath for about 3 hours. The mixture was allowed to stand for several days, then chilled and diluted with water. The solid which separated was collected, washed with water, then with 50% aqueous ethanol, and then with diethyl ether and dried in vacuo to give 3.8 g. of ethyl 4-methyl-4,5-dihydro-5-oxopyrazolo[1,5-a]quinazoline-3-carboxylate, m.p. 126°–129° C.

EXAMPLES 2A–2L

Following a procedure similar to that described in Example 2 above, substituting for the ethyl 4,5-dihydro-5-oxopyrazolo[1,5-a]quinazoline-3-carboxylate used therein an appropriate ethyl 7- or 8-$R_3$-4,5-dihydro-5-oxopyrazolo[1,5-a]quinazoline-3-carboxylate, the following compounds of formulat I were similarly prepared where, in each case, $R_1$ is $C_2H_5$.

Table 2

| Example | $R_2/R_3$ | Wt.S.M./Wt.Prod. | m.p.(°0 C.)/Solv. |
|---|---|---|---|
| 2A | $C_2H_5$ | 12.9 | (a) |
|  | H | 13.5 |  |
| 2B | $CH_2CH=CH_2$ | 12.9 | (a) |
|  | H | 14.2 |  |
| 2C | $CH_2$-cyclopropyl | 12.9 | (a) |
|  | H | 16.0 |  |
| 2D | $CH_2CH(CH_3)=CH_2$ | 12.9 | (a) |
|  | H | 18.0 |  |
| 2E | $CH_2CH=C(CH_3)_2$ | 12.9 | (a) |
|  | H | 15.0 |  |
| 2F | $CH_3$ | 4.4 | 140–141 |
|  | 7-$CH_3$ | 4.3 | DMF/water |
| 2G | $CH_3$ | 44.3 | 132–134 |
|  | 8-$CH_3$ | 44.7 | DMF/water |
| 2H | $CH_3$ | 20.0 | 159–161 |
|  | 7-Cl | 20.2 | tetrahydrofuran |
| 2J | $CH_3$ | 11 | 150–155 |
|  | 8-Cl | 10.7 | DMF/water |
| 2K | $CH_3$ | 29.5 | 134–137 |
|  | 7-F | 30 | DMF/water |
| 2L | $CH_2CH=CH_2$ | 8.8 | (a) |
|  | 7-F | 9.4 |  |

(a) The crude ester obtained was not purified but was saponified to the free acid. See Examples 7A, 7B, 7C, 7D, 7E and 7Q.

EXAMPLE 3

A sample of 20 g. (0.28 mole) of ethyl 4-methyl-4,5-dihydro-5-oxopyrazolo[1,5-a]quinazoline-3-carboxylate was placed in a round bottomed flask and covered with bromine. The flask was covered and allowed to stand for several days. The bromine was then allowed to evaporate, the solid residue was ground and heated on a steam bath in an open dish to free it of bromine and hydrogen bromide and recrystallized from tetrahydrofuran to give 18.2 g. of ethyl 7-bromo-4-methyl-4,5-dihydro-5-oxopyrazolo[1,5-a]quinazoline-3-carboxylate, m.p. 155°–157° C.

EXAMPLE 4

To a solution of 9.1 g. (0.034 mole) of ethyl 4-methyl-4,5-dihydro-5-oxopyrazolo[1,5-a]quinazoline-3-carboxylate in 50 ml. of concentrated sulphuric acid at ambient temperature was added 3.0 g. (0.035 mole) of powdered sodium nitrate and the suspension was stirred for about 30 minutes during which time the salt slowly dissolved and the solution turned orange. The solution was then poured onto ice, and the yellow solid which separated was collected by filtration, washed with isopropanol and then recrystallized from DMF to give 7.2 g. of ethyl 4-methyl-7-nitro-4,5-dihydro-5-oxopyrazolo[1,5-a]quinazoline-3-carboxylate, m.p. 206°–207° C.

EXAMPLE 5

To a solution of 45 g. (0.014 mole) of ethyl 4-methyl-7-nitro-4,5-dihydro-5-oxopyrazolo[1,5-a]quinazoline-3-carboxylate in 25 ml. of absolute ethanol and 3 teaspoons of Raney nickel was added dropwise 20 ml. of 100% hydrazine hydrate while refluxing the mixture. The mixture was allowed to stand for about 12 hours, then filtered, and the filtrate was evaporated to dryness in vacuo. Recrystallization of the residue from DMF gave 28.1 g. of ethyl 7-amino-4-methyl-4,5-dihydro-5-oxopyrazolo[1,5-a]quinazoline-3-carboxylate, m.p. 227°–230° C.

EXAMPLE 6

A solution of 5 g. (0.018 mole) of ethyl 7-amino-4-methyl-4,5-dihydro-5-oxopyrazolo[1,5-a]quinazoline-3-carboxylate and 2.4 g. (0.018 mole) of phenyl isothiocyanate in 250 ml. of pyridine was stirred and heated on a steam bath for about 2 hours, then cooled and diluted with water. The solid which separated was collected to give crude ethyl 4-methyl-7-phenylthioureido-4,5-dihydro-5-oxopyrazolo[1,5-a]quinazoline-3-carboxylate which was not further purified but used as such in Example 7T.

EXAMPLE 7

About 0.05 mole of ethyl 4-methyl-4,5-dihydro-5-oxopyrazolo[1,5-a]quinazoline-3-carboxylate was suspended in ethanol and treated while hot with a 10 percent solution of aqueous sodium hydroxide. The mixture was warmed until a clear solution formed and then filtered. The filtrate was neutralized with glacial acetic acid followed by dilute hydrochloric acid, and the solid which separated was collected, washed with water and dried to give 10.7 g. of 4-methyl-4,5-dihydro-5-oxopyrazolo[1,5-a]quinazoline-3-carboxylic acid, m.p. 230°–231° C.

EXAMPLE 7A–7T

Following a procedure similar to that described in Example 7 above, substituting for the ethyl 4-methyl-4,5-dihydro-5-oxopyrazolo[1,5-a]quinazoline-3-carboxylate used therein an appropriate ethyl 4-$R_2$-7- or 8-$R_3$-4,5-dihydro-5-oxopyrazolo[1,5-a]quinazoline-3-carboxylate, the following compounds of formula I given in Table 7 were prepared where, in each case, $R_1$ is hydrogen.

Table 7

| Example | $R_2/R_3$ | Wt.S.M./Wt.Prod. | m.p.(° C.)/Solv. |
|---|---|---|---|
| 7A | $C_2H_5$ | 13.5 | 217–218 |
|  | H | 7.5 | ethanol |
| 7B | $CH_2CH=CH_2$ | 14.2 | 211–212 |
|  | H | 10.0 | ethanol |
| 7C | $CH_2$-cyclopropyl | 16.0 | 238–239 |
|  | H | 8.0 | DMF/water |
| 7D | $CH_2C(CH_3)=CH_2$ | 18.0 | 213–214 |
|  | H | 8.8 | DMF/water |
| 7E | $CH_2CH=C(CH_3)_2$ | 15.0 | 221–222 |
|  | H | 10.3 | DMF/water |
| 7F | $CH_3$ | 15.0 | 278–280 |
|  | 7-$CH_3$ | 13.2 | ethanol/water |
| 7G | H | 15.0 | 297–300 |
|  | 8-$CH_3$ | 13.4 | ethanol/water |
| 7H | $CH_3$ | 10.0 | 248–250 |
|  | 7-$CH_3$ | 8.2 | ethanol/water |
| 7J | H | 10.0 | 290–295 |
|  | 7-Cl | 7.5 | ethanol/water |
| 7K | $CH_3$ | 10.0 | 260–261 |
|  | 7-Cl | 9.1 | ethanol/water |
| 7L | H | 8.0 | 308–310 |
|  | 8-Cl | 2.7 | DMF |
| 7M | $CH_3$ | 10.2 | 257–260 |
|  | 8-Cl | 4.4 | tetrahydrofuran |
| 7N | H | 15.0 | 336–340 |
|  | 7-Cl | 13.1 | ethanol/water |
| 7P | $CH_3$ | 15.0 | 249–253 |

Table 7-continued

| Example | R₂/R₃ | Wt.S.M./Wt.Prod. | m.p.(° C.)/Solv. |
|---|---|---|---|
| 7Q | 7-F<br>CH₂CH=CH₂ | 12.3<br>9.4 | ethanol/water<br>208–210 |
| 7R | 7-F<br>CH₃ | 5.0<br>10.0 | tetrahydrofuran<br>262(dec.) |
| 7S | 7-Br<br>CH₃ | 9.4<br>14.1 | ethanol/water<br>277–278 |
| 7T | 7-NO₂<br>CH₃<br>7-C₆H₅NHCSNH | 11.2<br>about 7.4<br>2.5 | DMF<br>203–205 |

EXAMPLE 8

To a solution of 6.5 g. (0.12 mole) of sodium methoxide in 500 ml. of absolute ethanol was added 27 g. (0.10 mole) of 4-(2-propenyl)-4,5-dihydro-5-oxopyrazolo[1,5-a]quinazoline-3-carboxylic acid (described above in Example 7B), and the mixture was heated until all material had dissolved. The mixture was then filtered through filter aid, the filtrate allowed to cool, and the solid which separated was collected, washed with absolute ethanol, then with ether and dried to give 20 g. of sodium 4-(2-propenyl)-4,5-dihydro-5-oxopyrazolo[1,5-a]quinazoline-3-carboxylate, m.p. 235°–238° C.

EXAMPLE 9

A mixture of 14.7 g. (0.06 mole) of 4-methyl-4,5-dihydro-5-oxopyrazolo[1,5-a]quinazoline-3-carboxylic acid, 9 g. (0.06 mole) of chloromethyl pivalate and 30 g. (0.3 mole) of powdered potassium bicarbonate in 75 ml. of anhydrous DMF was heated and stirred on a steam bath for about 3 hours, then cooled, diluted with ether to about 1 liter and filtered. The filtrate was washed five times with water, dried over magnesium sulphate, filtered and evaporated to dryness to give about 15 g. of pivaloyloxymethyl 4-methyl-4,5-dihydro-5-oxopyrazolo[1,5-a]quinazoline-3-carboxylate, m.p. 92°–94° C.

EXAMPLE 10

To a solution of 2 g. (0.0069 mole) of 4-methyl-7-nitro-4,5-dihydro-5-oxopyrazolo[1,5-a]quinazoline-3-carboxylic acid in a solution of 30 ml. of water and 12 ml. of ten percent potassium hydroxide solution was added Raney nickel followed by 1 ml. of 100 percent hydrazine hydrate. When bubbling had ceased, the catalyst was removed by filtration, and the clear filtrate was acidified with dilute hydrochloric acid. The solid which separated was collected, washed once with water, then with absolute ethanol, then with diethyl ether and dissolved in 50 ml. of hot DMF. The solution was diluted with 50 ml. of absolute ethanol, and the solid which separated was collected, washed with alcohol, then with diethyl ether and dried to give 1.2 g. of 7-amino-4-methyl-4,5-dihydro-5-oxopyrazolo[1,5-a]quinazoline-3-carboxylic acid, m.p. 268°–270° C.

BIOLOGICAL TEST RESULTS

Results obtained in rats in the carrageenin-edema test (CE) and the adjuvant arthritis test (AA) for the compounds of the invention are given in the table below. Here, and elsewhere in other tables which follow, compounds are identified by the Example number above where their preparations are recorded. For purposes of comparison, data are also given for the reference compound 4,5-dihydro-5-oxopyrazolo[1,5-a]quinazoline-3-carboxylic acid disclosed by Wright, ibid., identified here and elsewhere in the tables which follow as "Ref.".

| Example | Dose(mmole/kg.) | % Inhibition C.E. | % Inhibition A.A. |
|---|---|---|---|
| Ref. | .02 | — | 26 |
|  | .08 | 0 | 31 |
|  | .324 | 7 | 10 |
| 7 | .08 | — | 16 |
|  | .324 | 11 | 39* |
| 7A | .08 | — | 27* |
|  | .324 | 33** | — |
| 7B | .02 | — | 18 |
|  | .08 | 38* | 34 |
|  | .324 | 73** | 84** |
| 7C | .08 | 25** 28**(a) | — |
|  | .324 | 33** 26**(a) | 74** |
| 7D | .08 | 15 | — |
|  | .324 | 24** | 43** |
| 7E | .08 | 3 | — |
|  | .324 | 4 | 34* |
| 7P | .324 | 0 | — |
| 7Q | .08 | 0 | — |
|  | .324 | 4 | 72** |
| 8 | .02 | — | 29 |
|  | .08 | — | 47* |
|  | .09 | 20 | — |
|  | .324 | — | 80** |
|  | .36 | 31** | — |

*Statistically significant from carrageenin-injected controls at the p ≦ .05 level
**Statistically significant from carrageenin-injected controls at the p ≦ .01 level
(a) Results of two tests Results obtained in rats in the passive cutaneous anaphylaxis test for the compounds of the invention are given in the table below. Results are expressed either in terms of % Inhibition at a standard dose of 100 mg./kg. (p.o.), as an Average Effective Dose₅₀ (AED₅₀), or as a ratio, R, where:

$$R = \frac{\text{reciprocal of antibody dilution necessary for k mm. diam. in control group}}{\text{reciprocal of antibody dilution necesssary for k mm. dia. in medicated group}}$$

Compounds having R values from 1.0 to 2.0 are considered inactive; from 2.0 to 4.0 weakly active; from 4.0 to 8.0 moderately active; and >8.0 strongly active.

| Example | % Inhibition | AED₅₀ | R |
|---|---|---|---|
| Ref. | 62 | 2–15 | — |
| 1A | 63 | — | — |
| 1B | Inac. | — | — |
| 1C | 48 | — | — |
| 1E | Inac. | — | — |
| 2F | 6(Inac.) | — | — |
| 2G | 46 | — | — |
| 2H | 32 | — | — |
| 2K | — | — | 3.0 |
| 7 | 68 | — | — |
| 7A | 81 | 12 | — |
| 7B | 40 | — | — |
| 7C | — | — | 6.5 |
| 7D | — | — | 4.6 |
| 7E | — | — | 3.8 |
| 7F | 65 | — | — |
| 7G | — | ca. 15 | — |
| 7H | 73 | 34 | — |
| 7J | 92 | 5–10 | — |
| 7K | — | 9 | — |
| 7L | 74 | — | — |
| 7M | 56 | — | — |
| 7N | — | — | 3.8 |
| 7P | Inac. | — | — |
| 7R | 63 | — | — |
| 7S | — | 37 | — |
| 9 | — | — | 6.7 |

Results obtained in amoebacidal and trypanosomicidal tests on the compounds of the invention against *E. criceti* and *T. brucei*, respectively, are given in the table below. Results are expressed as a ratio: Number of Animals Cleared/Total Test Animals.

| Example | No. Cleared/No. Tested (Dose mg./kg.) | |
|---|---|---|
| | Amoeba | Tryp. |
| 2 | — | 2/5 (200/p.o., i.p.) |
| | | 0/5 (50/p.o., i.p.) |
| 2F | 5/5 (100) | — |
| | 0/5 (25) | |
| 2H | 2/4 (100) | — |
| 4 | 2/4 (100) | — |
| 7 | — | 5/5 (200/p.o. 2×/day × 4) |
| | | 0/5 (100/p.o. 2×/day × 4) |
| 7H | — | 10/10 (200/p.o, 2×/day × 4) |
| | | 4/5 (200/p.o., i.p.) |
| 7K | — | 2/4 (200/p.o., i.p.) |
| 7L | 2/5 (100) | — |
| 7M | — | 5/5 (200/p.o., i.p.) |
| 7P | Inac. | 3/5 (200/p.o., i.p.) |
| 7T | 3/3 (100) | Inac. |
| | 0/3 (50) | |
| 10 | 5/5 (100) | |
| | 0/5 (50) | |

I claim:

1. A compound having the formula:

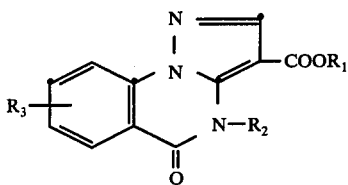

where:
$R_1$ is hydrogen or an alkali metal cation;
$R_2$ is methyl, ethyl, lower-alkenyl or cyclopropylmethyl; and
$R_3$ is hydrogen or 7- or 8-halo,
except that when $R_1$ is hydrogen and $R_2$ is methyl, $R_3$ is not 7-fluoro.

2. A compound having the formula:

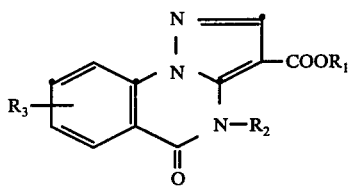

where:
$R_1$ is hydrogen, lower-alkyl or pivaloyloxymethyl;
$R_2$ is hydrogen, methyl, ethyl, lower-alkenyl or cyclopropylmethyl; and
$R_3$ is hydrogen, 7- or 8-methyl, 7- or 8-halo or 7-nitro, except that (a) when $R_1$ is lower-alkyl and $R_2$ is hydrogen, $R_3$ is not 8-methyl or 7-fluoro, (b) when $R_1$ is lower-alkyl and $R_2$ is methyl, $R_3$ is not 7-methyl or 7-bromo, (c) when $R_1$ is hydrogen and $R_2$ is methyl, $R_3$ is not 7-fluoro, and (d) when $R_1$ is hydrogen or lower-alkyl and $R_2$ is hydrogen, $R_3$ is not hydrogen.

3. A compound having the formula:

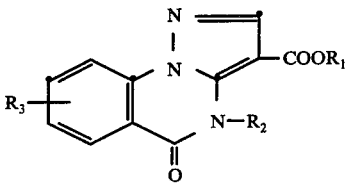

where:
$R_1$ is hydrogen or lower-alkyl;
$R_2$ is hydrogen or methyl; and
$R_3$ is hydrogen, 7-methyl, 7-nitro, 7-amino, 7- or 8-chloro, 7-fluoro or 7-phenylthioureido,
except that (a) when $R_1$ is hydrogen or lower-alkyl and $R_2$ is hydrogen, $R_3$ is not hydrogen or 7-fluoro, and (b) when $R_1$ is lower-alkyl and $R_2$ is methyl, $R_3$ is not amino.

4. A compound according to claim 1 where $R_2$ is methyl or ethyl.

5. A compound according to claim 1 where $R_2$ is loweralkenyl.

6. A compound according to claim 1 where $R_2$ is cyclopropylmethyl.

7. 4-Methyl-4,5-dihydro-5-oxopyrazolo[1,5-a]quinazoline-3-carboxylic acid according to claim 4.

8. 4-Ethyl-4,5-dihydro-5-oxopyrazolo[1,5-a]quinazoline-3-carboxylic acid according to claim 4.

9. 7-Fluoro-4-methyl-4,5-dihydro-5-oxopyrazolo[1,5-a]quinazoline-3-carboxylic acid according to claim 3.

10. 4-(2-Propenyl)-4,5-dihydro-5-oxopyrazolo[1,5-a]quinazoline-3-carboxylic acid according to claim 5.

11. Sodium 4-(2-propenyl)-4,5-dihydro-5-oxopyrazolo[1,5-a]quinazoline-3-carboxylate according to claim 5.

12. 7-Fluoro-4-(2-propenyl)-4,5-dihydro-5-oxopyrazolo[1,5-a]quinazoline-3-carboxylic acid according to claim 5.

13. 4-Cyclopropylmethyl-4,5-dihydro-5-oxopyrazolo[1,5-a]quinazoline-3-carboxylic acid according to claim 6.

14. 4-(2-Methyl-2-propenyl)-4,5-dihydro-5-oxopyrazolo[1,5-a]quinazoline-3-carboxylic acid according to claim 5.

15. 4-(3-Methyl-2-butenyl)-4,5-dihydro-5-oxopyrazolo[1,5-a]quinazoline-3-carboxylic acid according to claim 5.

16. A compound according to claim 2 where $R_1$ and $R_2$ are each hydrogen.

17. A compound according to claim 2 where $R_1$ is hydrogen and $R_2$ is methyl or ethyl.

18. A compound according to claim 2 where $R_1$ is hydrogen and $R_2$ is lower-alkenyl.

19. A compound according to claim 2 where $R_1$ is hydrogen and $R_2$ is cyclopropylmethyl.

20. A compound according to claim 2 where $R_1$ is lower-alkyl and $R_2$ is methyl or ethyl.

21. A compound according to claim 2 where $R_1$ is lower-alkyl and $R_2$ is lower-alkenyl.

22. A compound according to claim 2 where $R_1$ is lower-alkyl and $R_2$ is cyclopropylmethyl.

23. 7-Methyl-4,5-dihydro-5-oxopyrazolo[1,5-a]quinazoline-3-carboxylic acid according to claim 16.

24. 8-Methyl-4,5-dihydro-5-oxopyrazolo[1,5-a]quinazoline-3-carboxylic acid according to claim 16.

25. 7-chloro-4,5-dihydro-5-oxopyrazolo[1,5-a]quinazoline-3-carboxylic acid according to claim 16.

26. 8-Chloro-4,5-dihydro-5-oxopyrazolo[1,5-a]quinazoline-3-carboxylic acid according to claim 16.

27. 7-Fluoro-4,5-dihydro-5-oxopyrazolo[1,5-a]quinazoline-3-carboxylic acid according to claim 16.

28. 4,7-Dimethyl-4,5-dihydro-5-oxopyrazolo[1,5-a]quinazoline-3-carboxylic acid according to claim 17.

29. 7-Chloro-4-methyl-4,5-dihydro-5-oxopyrazolo[1,5-a]quinazoline-3-carboxylic acid according to claim 17.

30. 7-Bromo-4-methyl-4,5-dihydro-5-oxopyrazolo[1,5-a]quinazoline-3-carboxylic acid according to claim 17.

31. 4-Methyl-7-nitro-4,5-dihydro-5-oxopyrazolo[1,5-a]quinazoline-3-carboxylic acid according to claim 17.

32. Ethyl 7-fluoro-4-methyl-4,5-dihydro-5-oxopyrazolo[1,5-a]quinazoline-3-carboxylate according to claim 20.

33. Ethyl 4,8-dimethyl-4,5-dihydro-5-oxopyrazolo[1,5-a]quinazoline-3-carboxylate according to claim 20.

34. Ethyl 7-chloro-4-methyl-4,5-dihydro-5-oxopyrazolo[1,5-a]quinazoline-3-carboxylate according to claim 20.

35. Pivaloyloxymethyl 4-methyl-4,5-dihydro-5-oxopyrazolo[1,5-a]quinazoline-3-carboxylate according to claim 2.

36. A compound according to claim 3 where $R_1$ and $R_2$ are both hydrogen.

37. A compound according to claim 3 where $R_1$ is hydrogen and $R_2$ is methyl.

38. A compound according to claim 3 where $R_1$ is lower-alkyl and $R_2$ is hydrogen.

39. A compound according to claim 3 where $R_1$ is lower-alkyl and $R_2$ is methyl.

40. 8-Chloro-4-methyl-4,5-dihydro-5-oxopyrazolo[1,5-a]quinazoline-3-carboxylic acid according to claim 37.

41. 7-Amino-4-methyl-4,5-dihydro-5-oxopyrazolo[1,5-a]quinazoline-3-carboxylic acid according to claim 37.

42. 4-Methyl-7-phenylthioureido-4,5-dihydro-5-oxopyrazolo[1,5-a]quinazoline-3-carboxylic acid according to claim 37.

43. Ethyl 7-methyl-4,5-dihydro-5-oxopyrazolo[1,5-a]quinazoline-3-carboxylate according to claim 38.

44. Ethyl 7-chloro-4,5-dihydro-5-oxopyrazolo[1,5-a]quinazoline-3-carboxylate according to claim 38.

45. Ethyl 4-methyl-7-nitro-4,5-dihydro-5-oxopyrazolo[1,5-a]quinazoline-3-carboxylate according to claim 39.

46. Ethyl 4,7-dimethyl-4,5-dihydro-5-oxopyrazolo[1,5-a]quinazoline-3-carboxylate according to claim 39.

47. Ethyl 4-methyl-4,5-dihydro-5-oxopyrazolo[1,5-a]quinazoline-3-carboxylate according to claim 39.

48. Ethyl 8-methyl-4,5-dihydro-5-oxopyrazolo[1,5-a]quinazoline-3-carboxylate.

49. Ethyl 7-fluoro-4,5-dihydro-5-oxopyrazolo[1,5-a]quinazoline-3-carboxylate.

50. Ethyl 7-bromo-4-methyl-4,5-dihydro-5-oxopyrazolo[1,5-a]quinazoline-3-carboxylate.

51. Ethyl 7-amino-4-methyl-4,5-dihydro-5-oxopyrazolo[1,5-a]quinazoline-3-carboxylate.

52. A composition for the treatment of allergic conditions comprising a pharmaceutical carrier together with an anti-allergically effective amount of a compound having the formula:

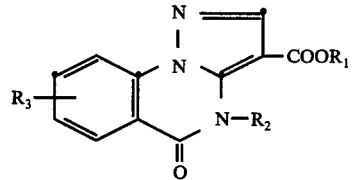

where:

$R_1$ is hydrogen, lower-alkyl or pivaloyloxymethyl;

$R_2$ is hydrogen, methyl, ethyl, lower-alkenyl or cyclopropylmethyl; and $R_3$ is hydrogen, 7- or 8-methyl, 7- or 8-halo or 7-nitro, except that (a) when $R_1$ is lower-alkyl and $R_2$ is hydrogen, $R_3$ is not 8-methyl or 7-fluoro, (b) when $R_1$ is lower-alkyl and $R_2$ is methyl, $R_3$ is not 7-methyl or 7-bromo, and (c) when $R_1$ is hydrogen and $R_2$ is methyl, $R_3$ is not 7-fluoro.

53. A composition according to claim 52 wherein the active ingredient is 4,5-dihydro-5-oxopyrazolo[1,5-a]quinazoline-3-carboxylic acid.

* * * * *

UNITED STATES PATENT AND TRADEMARK OFFICE
CERTIFICATE OF CORRECTION

PATENT NO. : 4,105,766
DATED : August 8, 1978
INVENTOR(S) : E. John Alexander

It is certified that error appears in the above-identified patent and that said Letters Patent are hereby corrected as shown below:

Column 1, line 28, change "of" to read -- or --.

Column 2, line 5, change "7-fluoro." to read --7-fluoro,--.

Column 4, line 48 change "three of four" to read --three or four--.

Signed and Sealed this

Seventeenth Day of August 1982

[SEAL]

Attest:

Attesting Officer

GERALD J. MOSSINGHOFF

Commissioner of Patents and Trademarks